US006540356B1

(12) United States Patent
He

(10) Patent No.: US 6,540,356 B1
(45) Date of Patent: Apr. 1, 2003

(54) INSTRUMENT AND A METHOD FOR MEASURING ABERRATION OF HUMAN EYES

(76) Inventor: Jicang He, Institute of Psychology, Academia Sinica, Deshengmenwai, Beishatan District, Beijing 100101 (CN)

(*) Notice: Subject to any disclaimer, the term of this patent is extended or adjusted under 35 U.S.C. 154(b) by 0 days.

(21) Appl. No.: 09/856,151

(22) PCT Filed: Oct. 10, 1999

(86) PCT No.: PCT/CN99/00160

§ 371 (c)(1),
(2), (4) Date: Jul. 30, 2001

(87) PCT Pub. No.: WO00/32086

PCT Pub. Date: Aug. 6, 2000

(30) Foreign Application Priority Data

Dec. 2, 1998 (CN) ........................ 98125083 A

(51) Int. Cl.⁷ ................................. A61B 3/10
(52) U.S. Cl. ..................................... 351/211
(58) Field of Search ................. 351/200, 205, 351/211, 213, 220, 221, 246; 600/425, 476

(56) References Cited

U.S. PATENT DOCUMENTS

| 5,475,452 A | * | 12/1995 | Kuhn et al. ................. 351/221 |
| 5,592,246 A | * | 1/1997 | Kuhn et al. ................. 351/221 |
| 5,873,832 A | * | 2/1999 | Maloney et al. ............. 351/207 |
| 6,206,522 B1 | * | 3/2001 | Maloney et al. ............. 351/205 |

* cited by examiner

Primary Examiner—Marvin M. Lateef
Assistant Examiner—John R. Sanders
(74) Attorney, Agent, or Firm—Rosenberg, Klein & Lee

(57) ABSTRACT

The present invention discloses an apparatus and a method for measuring aberrations in the human eye by utilizing the tracking of rays of light to measure the aberration in the human eye. The displacement of the incident light with respect to the ideal point position in the eye is corrected by changing the incident angle of the incident light so as to superimpose with the ideal light point. The variation of the incident light is analyzed by least mean square procedure so as to obtain the two-dimensional wave aberration profile and the magnitudes of independent aberrations. The apparatus comprises light sources, optical system, means for changing the incident position of the incident light, means for changing the incident angle of the incident light, and computer control means.

7 Claims, 2 Drawing Sheets

INSTRUMENT AND A METHOD FOR MEASURING ABERRATION OF HUMAN EYES

BACKGROUND OF THE INVENTION

1. Field of the Invention

The present invention generally relates to an equipment for checking human eyes in medical use, and more particularly, to an apparatus and a method for measuring aberrations in the human eye.

2. Description of the Prior Art

The human eye is considered as an optical system for image formation, which forms the image of an object being viewed on the retina of the eye and provides the nerve system with the image, so as to obtain a visual signal. An ideal human eye is capable of forming the image of an object sharply on the retina, on which the contrast of brightness distribution on the surface remains unchanged. Meanwhile, the lights emitted (or reflected) from a certain point of the surface of an object through the pupil of the eye focus on a corresponding point on the retina. In real lives, however, the human eye is not ideal, and the lights through the pupil form a spot instead of a focal point. Only in a few cases the light rays reach the ideal point, while in most of the cases the lights do not. The optical path divergence due to the fore-mentioned failure of an optical system is referred to as aberration, which causes the formed image to be out of focus and degrades the eyesight.

There are two approaches for describing the aberration characteristics. One is based upon a two-dimensional aberration profile, i.e., the wave aberration profile, where a set of coordinates with an origin at the center is established on the pupil of the human eye. The aberrations with respect to all the rays of light through the pupil are recorded according to the incident points. It has advantage that the aberration profile can be recorded in detail, but has disadvantage for being too complicated and too irregular to describe. The other approach is to sum up all the simple independent aberrations according to the individual weights so as to obtain an overall aberration. Such an overall aberration is uniquely determined as long as the independent aberrations are determined.

Aberrations degrade the sight. Therefore, it is necessary to correct the aberrations in order to improve the sight. Since only short-sightedness/far-sightedness and astigmatism can be determined by the conventional optometry technique, correction techniques such as wearing glasses and laser operation can only be applicable to corrections for being out of focus and astigmatism. On the other hand, the short-sighted/far-sighted or astigmatistic patients often have other more serious aberrations, which cannot be completely determined and accordingly corrected. Therefore, the sight cannot be greatly improved even by wearing glasses or laser operation.

To date, the aberration measuring techniques capable of providing the wave aberration profile and analysis of a plurality of independent aberrations are only available in the research stage. The apparatuses conventionally used for aberration measuring cannot provide both the wave aberration profile and the magnitudes of the components of independent aberrations. An new apparatus for measuring aberrations, (described in Journal of Optical Society of American, 1998, Vol. A15, No. 9, pp. 2449 %C pp. 2456) provides both the wave aberration profile and th magnitudes of the components of the independent aberrations within the 7th degree without mydriasis. This new apparatus is easier to use than another one (as described in Journal of Optical Society of American, 1997, Vol. A14, pp. 2873 "C pp. 2883), which can also provide both the wave aberration profile and the magnitudes of the components of the independent aberrations. However, in the new apparatus, the incident angle of the incident light is varied by a high-precision reflector control system, which suffers from a high price and poor reliability. On the other hand, the variation angle of the reflector is limited to a dynamic range of only 4 diopter, and also suffers from disadvantages such as a complicated structure, poor reliability, a high demand for precision, a high fabrication cost, and not being applicable to conventional equipment.

The principle for measuring the aberrations is described hereinafter. A fine beam of parallel rays of light (with a diameter of 0.5 mm) emits from a certain position on the pupil into the eye and forms a light point as seen by the person. When the incident position of the rays of light up in the eye is changed without any aberration, the light point stays stable at the ideal position and no change of the light point will be observed. However, when there is plurality of aberrations in the eye, the light point will move away from the ideal position, according to the variation of the incident pupil location of the incident light. The extent to which the rays of light stray away depends on the characteristics and the magnitudes of aberration. Meanwhile, if a control channel is added to the fore-mentioned parallel rays of light to form a cross-shaped image in the eye, the center of the cross-shaped image and the ideal position of the light point of the parallel rays of light may superimpose. Therefore, the amount of displacement corresponding to the ideal point due to aberrations of the parallel rays of light can be measured by obtaining the variation of the position of the light point from the center of the cross-shaped image. Thus, displacement can be measured by transferring the measurement of aberrations.

However, the amount of displacement of the image in the eye is hard to measure directly and can be only obtained indirectly. For example, if the incident angle of the incident light is changed when the incident position of the incident light on the retina of the eye is fixed, the light point will change its position according to the incident angle of the light. If the light point is moved to the center of the cross-shaped image by using the controlling means, the variation will be proportional to the magnitudes of aberration of the light through the retina. Similarly, such measurement can be performed on other positions of the retina so as to obtain the profile of the variation of the incident angle, i.e., the overall refraction profile. According to the overall refraction profile, the overall wave aberration profile and the magnitudes of the independent components can be obtained by using least mean square procedure (LMS).

In the experiments employing the fore-mentioned principle for measuring aberration, the incident position and the incident angle of the incident rays of light are measured by using mechanical control means, such as a stepper motor to precisely control and work with the pupil limiting means and select the position. The precision of the stepper motor is crucial and which makes a higher fabrication cost. Moreover, such components are poor in seismic and temperature characteristics and thus are not suitable for use in apparatuses for measurement.

SUMMARY OF THE INVENTION

It is therefore a main object of the present invention to provide an apparatus and a method for measuring aberrations in the human eyes, which can determine both overall wave front aberration profile and a plurality of independent aberrations of a human eye. Such an apparatus has advantages in its simple structure, good reliability, and low fabrication cost. In order to achieve the foregoing object, the present invention provides an apparatus, comprising: light sources, optical system, means for changing the incident position of the incident light, means for changing the incident angle of the incident light, and computer control means, wherein said light source include a light source for measurement composed of a set of light-emitting diodes (LEDs) arranged in an two-dimensional array and a light source for illumination; wherein said optical system includes a measuring optical channel composed of a first lens, a first reflector, a transparent visual target on a liquid crystal display, a first beam-splitter and a second reflector; a control channel composed of a third lens and a fixed visual target between said light source for illumination and said first beam-splitter; and a integrated channel composed of a second beam-splitter, a second lens and a third reflector between said second reflector and the retina of the eye; wherein said means for changing the incident position of the incident light includes an LED driving circuit for lighting one of said LEDs in said array of said light source for measurement; wherein said means for changing the incident angle of the incident light includes a mouse for controlling the motion of said transparent visual target on the plane perpendicular to the direction of light propagation; wherein said computer control means is connected to said LED driving circuit, said mouse and said liquid crystal display.

Said integrated channel further comprises a pupil monitoring optical channel composed of a infrared light source, said integrated channel, a fourth lens, a charge-coupled device (CCD) camera and a monitor connected to said CCD camera, wherein said fourth lens, said charge-coupled device (CCD) camera and said monitor are arranged on the other side of said second beam-splitter in said integrated optical path.

Said fixed visual target in said control channel is a transparent film with a cross-shaped image.

Said second beam-splitter is a selective beam-splitter being fully reflective for visible light and fully transparent for infrared light.

Said set of light-emitting diodes in said light source for measurement includes 37 light-emitting diodes arranged in an octagonal array.

The present invention further comprises a one-dimensional micro moving station and refraction adjusting means composed of manual adjusting means for moving said moving station along the direction of light propagation, wherein said second reflector and said second beam-splitter are arranged on said one-dimensional micro moving station.

The present invention also provides a method for measuring aberrations in the human eye, characterized in that;
(1) said means for changing the incident position of the incident light composed of said LED driving circuit connected to said computer control means and said light-emitting diode array selectively lights any of said set of light-emitting diodes so as to change the incident position of the incident light on the pupil plane in a point-by-point manner;
(2) said means for changing the incident angle of the incident light composed of said liquid crystal display and said mouse connected to said computer control means connects said transparent visual target and said liquid crystal display, changes the position of said transparent visual target on said liquid crystal display by moving said mouse, and move the transparent hole of said transparent visual target to the center of the cross-shaped image of said control channel, so as to change the incident angle on the pupil plane of the incident light; and
(3) the amount of displacement of said transparent visual target is recorded by using said computer control means, so as to calculate the variation of the incident angle, and the overall wave aberration profile and more than one of the independent aberrations are obtained by least mean square procedure.

The present invention provides advantages in that:
(1) the precision of the sampled position on the pupil plane depends on the precision of the light-emitting diode array fabrication, which is easy to achieve;
(2) once the fabrication of the light-emitting diode array is completed, the precision lasts eternally, which avoids the problems due to precision degradation resulting from the aging of the mechanical parts;
(3) the design of optical channel makes use of the light source to a maximal extent;
(4) light-emitting diodes, instead of laser sources or other intensive light sources, are employed to simplify the light source configuration and reduce the fabrication cost;
(5) the electric circuits run fast and are easy for use in computer processing;
(6) the integrated apparatus composed of control circuits and light-emitting diodes is easy to be standardized and implemented;
(7) the transparent visual target on the liquid crystal display is controlled by moving the mouse so as to achieve the changing of the incident angle without changing the incident position and enlarge the dynamic range to 10 diopter with the same precision; and
(8) the apparatus is characterized in using optical channel containing 4 lenses arranged in the measuring optical channel, the control channel, the pupil monitoring optical channel, and the integrated optical channel, respectively, which provides a more simple but better design of optical channel than the prior art.

In the apparatus and a method for measuring aberrations in the human eye according to the present invention, the aberrations of the human eye can be measured by utilizing the tracking of rays of light to measure. The displacement of the incident light with respect to the ideal point position on the pupil of the eye is corrected by changing the incident angle of the incident light so as to superimpose with the ideal light point. The variation of the incident light is analyzed by least mean square so as to obtain the two-dimensional wave aberration profile and the magnitudes of independent aberrations.

BRIEF DESCRIPTION OF THE DRAWINGS

A better understanding of the present invention can be obtained when the following detailed description of the preferred embodiment is considered in conjunction with the following drawings in which.

DETAILED DESCRIPTION OF PREFERRED EMBODIMENTS

Figure 1:
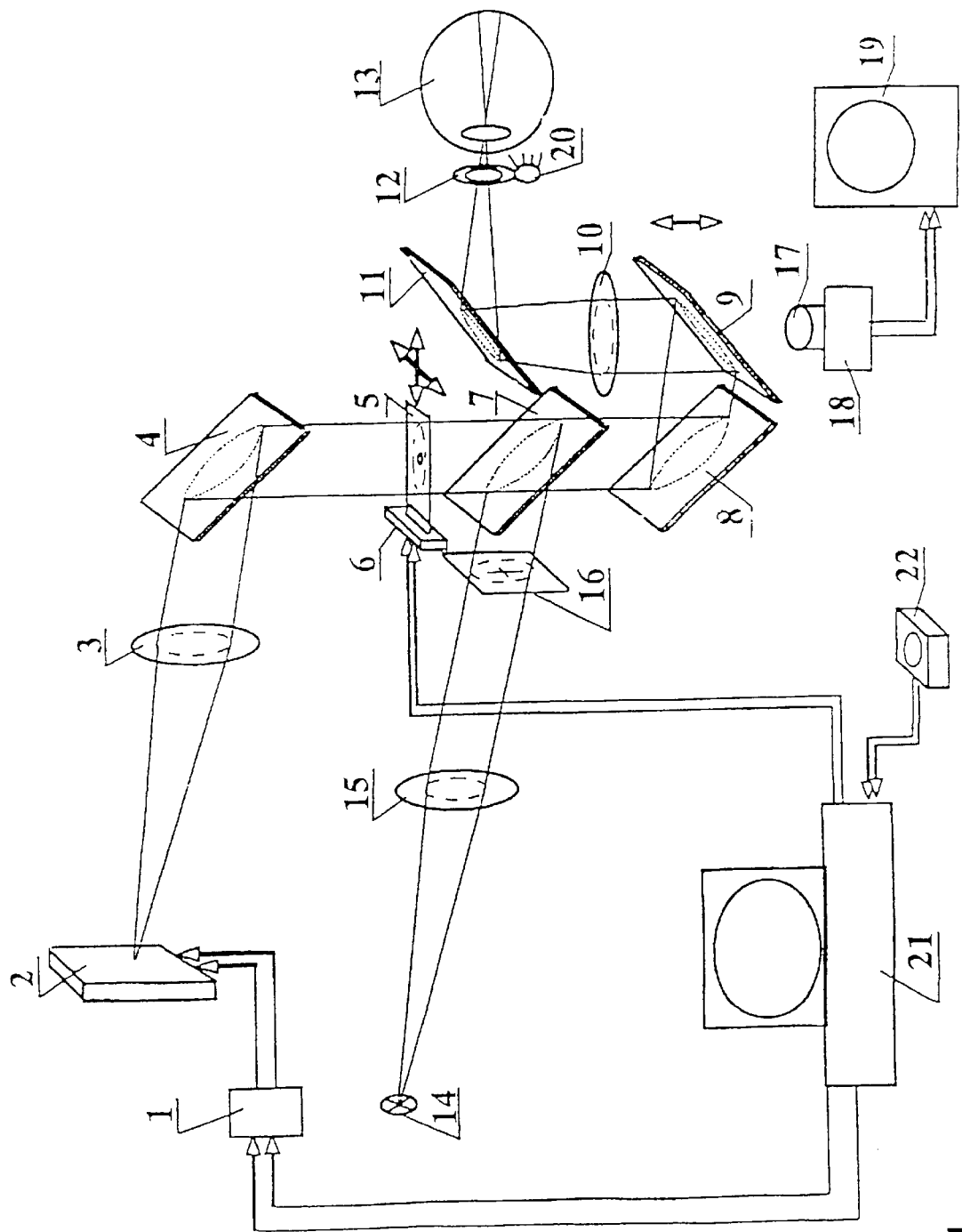
FIG. 1 is a schematic diagram illustrating an apparatus for measuring aberrations in the human eye according to the present invention.

Referring now to FIG. 1, which shows a schematic diagram illustrating an apparatus for measuring aberrations in the human eye according to the present invention. In the drawing, the apparatus comprises an light-emitting diode (LED) driving circuit 1, an LED array 2, a first lens 3, a first reflector 4, a transparent visual tag 5, a liquid crystal display 6, a first beam-splitter 7, a second reflector 8, a second beam-splitter 9, a second lens 10, a third reflector 11, an eyepiece frame 12, a light source for illumination 14, a third lens 15, a fixed visual tag 16, a fourth lens 17, a charge-coupled device (CCD) camera 18, a monitor 19, an infrared light source 20, computer control means 21, and a mouse 22. The number 13 indicates the human eye to be examined.

The LED driving circuit 1 is used for providing the measuring optical channel with light sources. It also selectively lights one light-emitting diode in an LED array 2. The measuring optical channel starts from an LED array 2 through a first lens 3, a first reflector 4, the transparent hole of a transparent visual target 5, a liquid crystal display 6, a first beam-splitter 7, a second reflector 8, a second beam-splitter 9, a second lens 10, a third reflector 11, and an eyepiece frame 12 to the eye 13. Since the terminal surface of the LED array 2 is positioned at the front focus plane of the first lens 3, the rays of light from each of the light-emitting diode become parallel after passing the first lens 3. The pupil plane of the human eye 13 is positioned at the rare focus plane of the second lens 10, therefore the second lens 10 focuses the parallel rays of light on the pupil plane. In this manner, the terminal surface of the LED array 2 is conjugate to the pupil plane of the eye 13. When a light-emitting diode is selectively lighted, the light emits through a certain position on the pupil plane into the human eye 13. In this manner, the position of the incident light may be changed.

Each of the light-emitting diode in the LED array 2 has a diameter of 0.5 mm preferably. The required number of the light-emitting diodes can be determined by the precision for measurement, preferably 37 light-emitting diodes. The focus length of the first lens 3 and the focus length of the second lens 10 can be the same or not. However, the diameter of the image of the terminal surface of the LED array 2 formed on the pupil of human eye 13 should be maintained within 6 to 8 mm. The transparent hole of the transparent visual target 5 has a diameter of 0.5 mm and is positioned at the front focus plane of the second lens 10, so as to be conjugate with the human eye 13.

The transparent visual tag 5 is placed on the liquid crystal display 6. The transparent visual tag 5 is perpendicular to the direction of light propagation and can move on the two-dimensional plane, manually controlled by using the computer control means 21 and the mouse 22. Meanwhile, the amount of displacement of the transparent visual tag 5 can be obtained by the computer control means 21. When the owner of the examined eye moves the mouse 22, the transparent visual target 5 is driven to move on the two-dimensional plane. In other words, when the incident angle of the incident light at some position is changed, the owner of the examined eye sees the displacement of the image of the light point formed by the transparent hole of the transparent visual target 5. The amount of displacement of the image of the light point with respect to the ideal light point is the aberration being measured. The recorded amount of displacement by the computer control means 21 is transferred into the variation of the incident angle and is further analyzed by least mean square to obtain the overall aberration profile and at least 30 independent aberrations.

The control channel starts from the light source for illumination 14 and is transferred into parallel rays of light by the third lens 15 onto the fixed visual target 16. The fixed visual target 16 is a transparent film with a cross-shaped image. The fixed visual target 16 remains fixed. The center of the cross-shaped image provides an ideal light point for aberration measurement. The owner of the examined eye only has to move the transparent visual target 5 by using the mouse 22 so as to change the incident angle of the incident light at some position and move the light point to the center of the cross. The control channel and the measuring optical channel merges after passing the beam-splitter 7.

The pupil monitoring optical channel includes an infrared light source 20, a fourth lens 17, a charge-coupled device (CCD) camera 18, and a monitor 19. The infrared light source 20 is arranged in the eyepiece frame 12. The infrared light source 20 illuminates the pupil of human eye 13 so as to form an image on the photosensitive face of the CCD camera by the second lens 10 and the fourth lens 17 after being reflected by the reflector 11. The pupil monitoring optical channel enters the integrated optical channel through the beam-splitter 9. The beam-splitter 9 is a selective beam-splitter being fully reflective for visible light and fully transparent for infrared light. The beam-splitter and the camera in the pupil monitoring optical channel construct a configuration for focus adjustment and monitoring.

In one embodiment, in order to let the visual target fix the reflector 8 and the beam-splitter 9 on a one-dimensional moving station (not shown) so as to allow them to move in parallel with the direction of light propagation, the owner of the examined eye manually controls the movement and changes the out-of-focus state of the system so as to allow continuous adjustment within a range of 4 diopter. Moreover, lenses of various focus lengths can be added to the eyepiece frame 12 to perform clarity compensation, so as to achieve the object of adjusting the focus within a large range.

Figure 2:
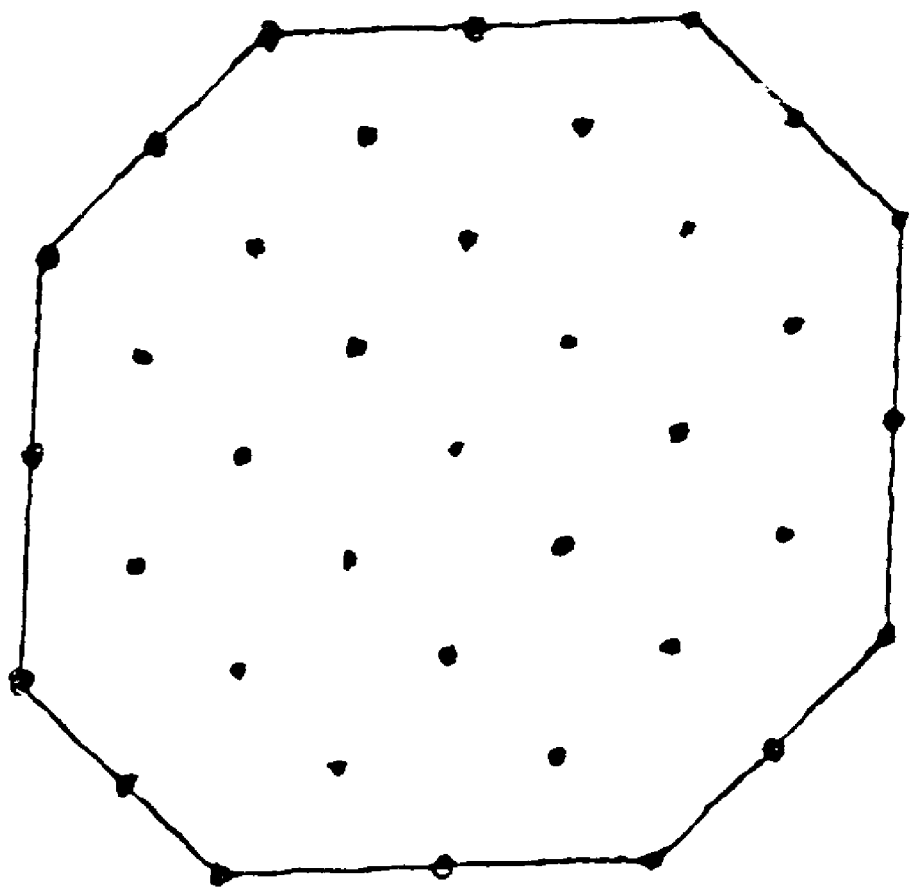
FIG. 2 is a schematic diagram illustrating an array of light-emitting diodes as shown in FIG. 1.

Please refer to FIG. 2, which shows a schematic diagram illustrating an array of light-emitting diodes as shown in FIG. 1. In the drawing, the terminal surface of the 37 light-emitting diodes forms a two-dimensional array of a regular octagon. The array is conjugate to the corresponding image formed by the lens. The computer control means 21 lights one or more of the light-emitting diodes by the LED driving circuit 1.

In accordance with the present invention, there is provided an apparatus and a method for measuring aberrations in the human eye, applicable to laser surgery in the eye, scientific research on short-sightedness/far-sightedness and general sight examining.

Although this invention has been disclosed and illustrated with reference to particular embodiments, the principles involved are susceptible for use in numerous other embodiments that will be apparent to persons skilled in the art. This invention is, therefore, to be limited only as indicated by the scope of the appended claims.

What is claimed is:

1. An apparatus for measuring aberrations in a human eye, comprising:

light sources, including a light source for measurement composed of a set of light-emitting diodes (LEDs) arranged in a two-dimensional array and a light source for illumination;

an optical system, including a measuring optical channel composed of a first lens, a first reflector, a transparent visual target on a liquid crystal display, a first beam-splitter and a second reflector, a control channel composed of a third lens and a fixed visual target between said light source for illumination and said first beam-splitter, and an integrated optical channel composed of a second beam-splitter, a second lens and a third reflector between said second reflector and the retina of the eye;

means for changing the incident position of the incident light, including an LED driving circuit for lighting one of said LEDs in said array of said light source for measurement;

means for changing the incident angle of the incident light, including a mouse for controlling the motion of said transparent visual target on the plane perpendicular to the direction of light propagation; and computer control means, connected to said LED driving circuit, said mouse and said liquid crystal display.

2. The apparatus of claim 1 wherein said optical channel further comprising a pupil monitoring optical channel, composed of a infrared light source, said integrated optical channel, a fourth lens, a charge-coupled device camera and a monitor connected to said charge-coupled device camera, wherein said fourth lens, said charge-coupled device camera and said monitor are arranged on the other side of said second beam-splitter in said integrated optical channel.

3. The apparatus of claim 1 wherein said fixed visual target in said control channel is a transparent film with a cross-shaped image.

4. The apparatus of claim 1 wherein said second beam-splitter is a selective beam-splitter being fully reflective for visible light and fully transparent for infrared light.

5. The apparatus of claim 1 wherein said set of light-emitting diodes in said light source for measurement includes 37 light-emitting diodes arranged in an octagonal array.

6. The apparatus of claim 1 further comprising a one-dimensional micro moving station and refraction adjusting means composed of manual adjusting means for moving said moving station along the direction of light propagation, wherein said second reflector and said second beam-splitter are arranged on said one-dimensional micro moving station.

7. A method for measuring aberrations in a human eye, the method comprising:

changing an incident position of incident light by use of an LED driving circuit connected to a computer control means and a light-emitting diode array which selectively lights any of said set of light-emitting diodes so as to change the incident position of the incident light on the pupil plane in a point-by-point manner;

changing an incident angle of the incident light by use of a liquid crystal display and a mouse connected to said computer control means which connects a transparent visual target and a liquid crystal display, changes the position of a transparent visual target on said liquid crystal display by moving said mouse, and moves a transparent hole of said transparent visual target to the center of a cross-shaped image of a control channel, so as to change the incident angle on the pupil plane of the incident light; and recording an amount of displacement of said transparent visual target by using said computer control means, so as to calculate a variation of the incident angle, and an overall wave aberration profile and more than one of an independent aberration are obtained by a least mean square procedure.

* * * * *